(12) United States Patent
Mulac et al.

(10) Patent No.: US 7,749,163 B2
(45) Date of Patent: Jul. 6, 2010

(54) UNIVERSAL SCISSORS JOINT APPARATUS

(75) Inventors: Anthony J. Mulac, East Jordan, MI (US); Daniel K. Farley, Traverse City, MI (US)

(73) Assignee: Peak Performance Company, Traverse City, MI (US)

( * ) Notice: Subject to any disclaimer, the term of this patent is extended or adjusted under 35 U.S.C. 154(b) by 1032 days.

(21) Appl. No.: 11/359,052

(22) Filed: Feb. 22, 2006

(65) Prior Publication Data

US 2006/0142644 A1  Jun. 29, 2006

Related U.S. Application Data

(63) Continuation of application No. 10/365,822, filed on Feb. 13, 2003, now abandoned, which is a continuation-in-part of application No. 10/164,487, filed on Jun. 6, 2002, now abandoned.

(51) Int. Cl.
*A61B 1/32* (2006.01)
(52) U.S. Cl. ..................................... 600/234
(58) Field of Classification Search ................. 600/184, 600/201, 218–219, 225–228, 230–234; 403/384, 403/385, 389, 391, 396, 398
See application file for complete search history.

(56) References Cited

U.S. PATENT DOCUMENTS

| | | | | |
|---|---|---|---|---|
| 5,727,899 A | * | 3/1998 | Dobrovolny | ................ 403/389 |
| 6,277,119 B1 | * | 8/2001 | Walulik et al. | ................ 606/57 |
| 6,736,775 B2 | * | 5/2004 | Phillips | ...................... 600/234 |

* cited by examiner

*Primary Examiner*—Anu Ramana
(74) *Attorney, Agent, or Firm*—McAndrews, Held & Malloy, Ltd.

(57) ABSTRACT

A universal joint apparatus comprises clamps, a locking mechanism, and a rod connecting the clamps and the locking mechanism. At least one clamp is a scissors clamp, i.e. a clamp comprising two segments fastened by a pivot. The scissors clamp generates extra compressive force on the object being held, providing a stable and rigid universal joint. Clamps are able to rotate with respect to each other, allowing for greater flexibility in usage. The universal joint apparatus is capable of being added to a support frame between other components. In one embodiment of the invention, the universal joint includes a dedicated retractor blade handle to ensure that the locked position of the cam handle is oriented substantially away from the operative site.

24 Claims, 8 Drawing Sheets

UNIVERSAL SCISSORS JOINT APPARATUS

RELATED APPLICATION

This application is a continuation of application Ser. No. 10/365,822, filed on Feb. 13, 2003, now abandoned, which is a continuation-in-part of application Ser. No. 10/164,487, filed Jun. 6, 2002, now abandoned. The foregoing applications are hereby incorporated by reference herein in their entirety, including the specification, claims, drawings and abstract.

BACKGROUND OF THE INVENTION

The present invention relates to surgical apparatus for retracting a patient's anatomy during an operation to provide exposure of the operative site. More particularly, the present invention relates to a universal scissors joint apparatus that is sturdy, stable, readily adjustable, and easily sterilized.

Surgical operations often require prolonged access to the internal anatomy of a patient. Retractors are used to hold back tissue around the surgical site, granting the surgeon the needed access. While hand-held retractors may be used during surgeries, it is often desirable to use mechanically mounted retractors.

Mechanical retractors are typically mounted to some kind of support structure. This support structure often takes the form of a frame surrounding part or all of the operating table. The frame may contain rails to which clamps may be attached. These clamps may connect the frame directly to a retractor, or to accessory rails to which retractors or additional rails may be connected. Greater flexibility in universal joint clamps alleviates some of the deficiencies of previous rail clamps in comparison to the manual application of retractors.

Universal joints must be sterilized before being brought into the operating area. Many previous universal joints have separable components which require more care and effort for sterilization due to the need to disassemble and reassemble the components. Universal joints with unitary designs permit sterilization without the need to disassemble the joints.

Some previous universal joints have used threaded locking mechanisms, which require lubrication and maintenance. Cam locking mechanisms require less maintenance and provide a much easier and more effective system for locking and unlocking the clamps.

Cam locking universal joints typically incorporate a cam handle to open and lock the universal joint's locking mechanism. Unfortunately, the manipulation of the cam locking mechanism often results in the cam handle being oriented towards, and into, the operative site, thereby potentially interfering with a surgeon's visual access to the patient's anatomy or physically intruding with a surgeon's movement. For example, U.S. Pat. No. 5,888,197 ("'197"), and U.S. Pat. No. 6,017,008 ("008") disclose floating cam handles that allow for the positioning of the cam handle at various orientations about the operative site and in relation to other support structure components. However, this freedom of movement may create unnecessary obstacles for the surgeon or create an additional issue that a surgical staff must consider and address. More specifically, in preparing for an operation, or while making adjustments during surgery, the fact that a cam handle was positioned into the field of operation, or at some other physically intrusive position, may be overlooked and impracticable to rectify.

U.S. Pat. No. 5,727,899 ("'899") teaches a unitary universal joint, wherein the cam handle may be substantially parallel to the handle of a retractor blade. However, because the retractor blade handle is removable, the handle, and associated retractor blade, may be inserted into the clamping member in a direction that allows the locking position of the cam handle to extend towards the operative site. Furthermore, the lack of an integrated retractor blade handle increases the difficulty and time required for setting up and positioning the retractor blade relative to the patient's anatomy.

Because other components may be secured to the frame, it is desirable for a universal joint to have the capability of being added to the frame between secured components.

While universal joints with the above features have been designed, it is desirable to have a universal joint with even greater ease of use, flexibility, stability, and rigidity.

It is also desirable to have a universal joint that is designed so as to ensure that the cam handle of the cam locking mechanism is oriented away from the operative site.

Furthermore, it is desirable to improve the efficiency and ease of setting up a retraction system by reducing the number of individual components that must be independently added to the universal joint.

BRIEF SUMMARY OF THE INVENTION

The present invention provides a universal joint apparatus. The present invention comprises clamps, a locking mechanism, and a rod associating the clamps with the locking mechanism. At least one clamp is a scissors clamp, i.e. a clamp comprising a first segment and a second segment, with the segments fastened by a pivot. The scissors clamp generates extra compressive force on the object being held, providing a stable and rigid universal joint. Clamps are able to rotate with respect to each other, allowing for greater flexibility in usage. The present invention is capable of being added to a support frame between other components. In one embodiment of the invention, the universal joint apparatus includes an integrated retractor blade handle, which, in conjunction with the cam locking mechanism, ensures that the locked position of the cam handle is oriented substantially away from the operating field.

These and other features, aspects, and advantages of the present invention will be better understood with reference to the accompanying drawings, descriptions, and claims.

Figure 1:
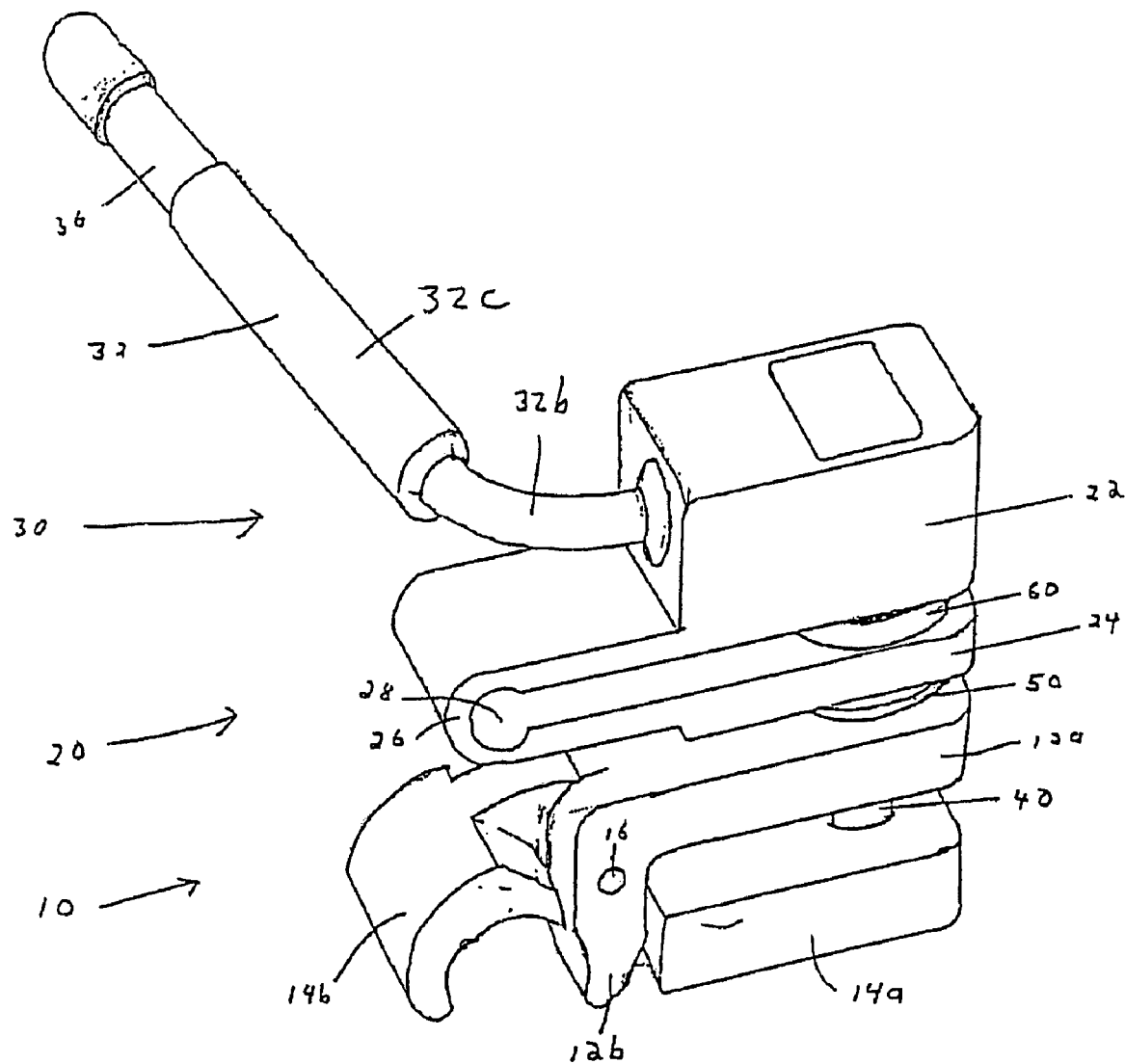
FIG. 1 is a top perspective view of an embodiment of the present invention.

The foregoing summary, as well as the following detailed description of the preferred embodiments of the present invention, will be better understood when read in conjunction with the appended drawings. For the purpose of illustrating the preferred embodiments of the present invention, there is shown in the drawings, embodiments which are presently preferred. It should be understood, however, that the present invention is not limited to the arrangements and instrumentality shown in the attached drawings.

DETAILED DESCRIPTION OF THE INVENTION

Figure 10:
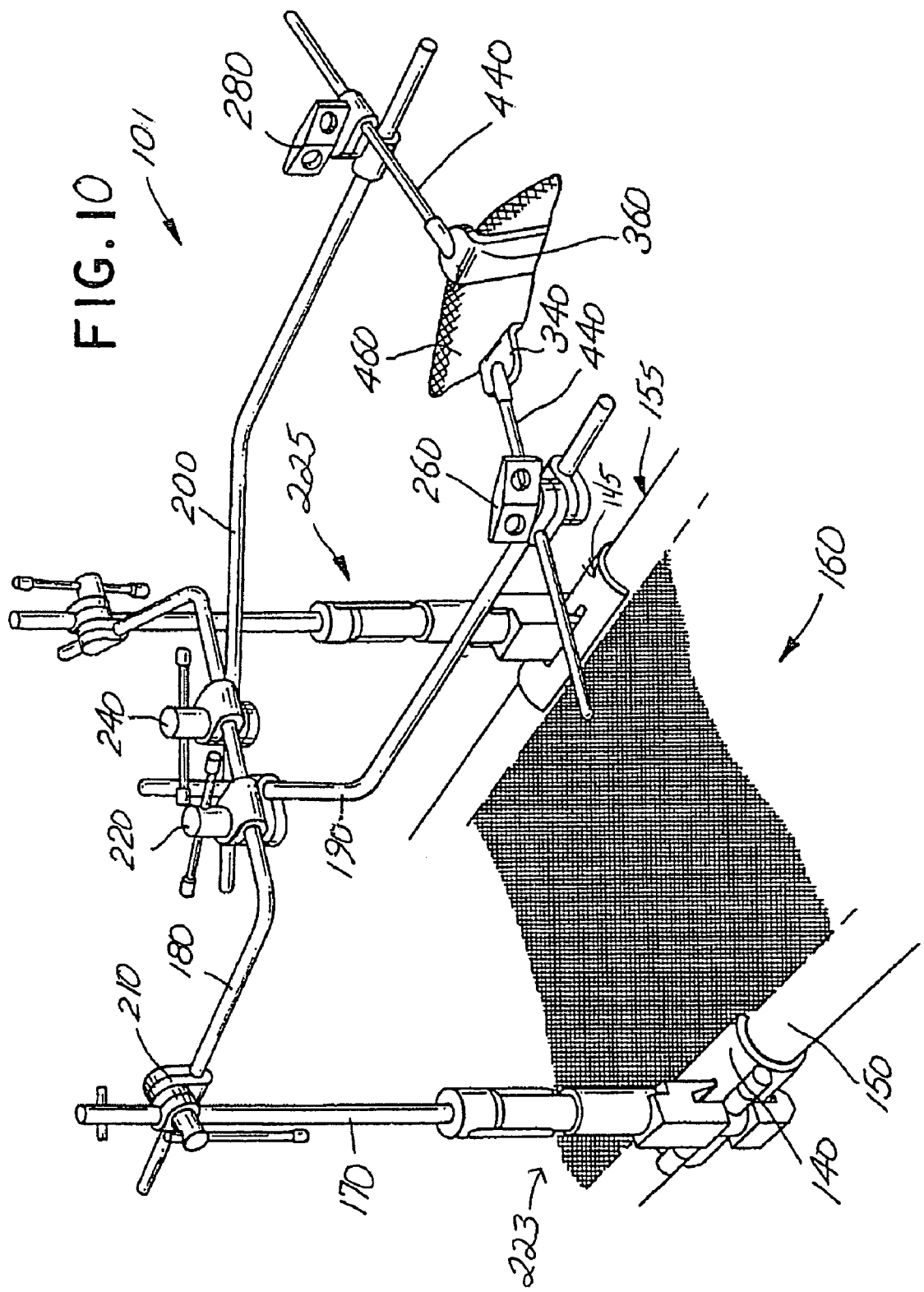
FIG. 10 illustrates the use of a conventional surgical retraction system.

FIG. 10 illustrates the use of conventional universal joints in a surgical retraction system 101. Adjustable clamps 223, 225 are secured, through the use adapters 140, 145, to the frames 150, 155 of a conventional framed stretcher 160. A post 170 extends vertically from a clamp 223 to provide support for a cross bar 180, which in turn provides support for a pair of extension arms 190, 200. The crossbar 180 is secured to the post 170 by a universal joint clamp 210. The extension arms 190, 200 are secured to the cross bar 180 by a pair of universal joint clamps 220, 240. Additional universal joint clamps 260, 280 are disposed along the extension arms 190, 200 for rigidly securing any number of retractor blades 340, 360 to the extension arms 190, 200.

The universal joints 260, 280 allow for both the rotation of the clamping mechanism along the longitudinal axis of the extension arms 190, 200 and the pivotable placement of the retractor blade handle 440 in relation to the extension arms 190, 200. The surgeon is then able to place the retractor blades 340, 360 at their desired position in the incision 460 made by the surgeon. The retractor blades 340, 360 are then used to retract the patient's anatomy, thereby making the incised opening accessible to the surgeon.

Referring to FIG. 1, the disclosed embodiment of the universal scissors joint apparatus includes a first clamping member referred to as a scissors clamp 10, a second clamping member referred to as a circle clamp 20, a cam locking mechanism 30, and a rod 40. The rod 40 associates the cam locking mechanism 30, the circle clamp 20, and the scissors clamp 10.

Figure 2:
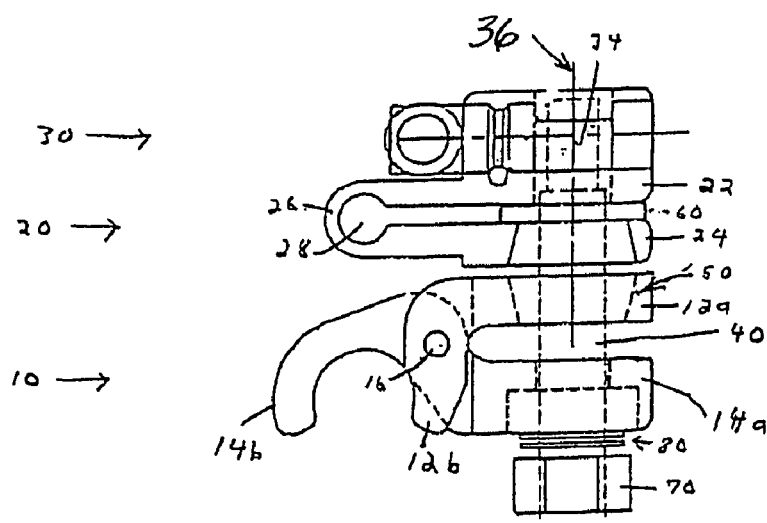
FIG. 2 is a partial bottom perspective view of the present invention.
Figure 3:
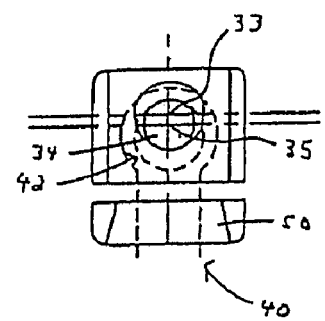
FIG. 3 is a side view, in partial cross-section of an embodiment of the present invention.

Referring to FIGS. 1, 2, and 3, the scissors clamp 10 includes two segments connected at a pivot 16, similar to a scissors, so that the two segments cross each other at the pivot 16. The first segment 12 includes an upper portion, referred to as an upper handle 12a, of the scissors clamp 10 proximal of the pivot 16 and engaging the rod 40; the first segment 12 further includes two lower portions, referred to as lower grippers 12b, of the scissors clamp 10 distal of the pivot 16. The second segment 14 includes a lower portion, referred to as a lower handle 14a, of the scissors clamp 10 proximal of the pivot 16; the second segment 14 further includes an upper portion, referred to as an upper gripper 14b, of the scissors clamp 10 distal of the pivot 16. The grippers 12b, 14b of the scissors clamp 10 are shaped so as to contour the surface of the object (not shown) to which the clamp is being attached. The inner surface of the upper gripper 14b of the scissors clamp 10 may include indentations 14c. These indentations 14c may be located opposite the lower grippers 12b. The handles 12a, 14a of the scissors clamp 10 are separated by a gap that allows the scissors clamp 10 to be squeezed, creating a tighter grip on the instrument being held by the grippers 12b, 14b of the clamp. The handles 12a, 14a of the scissors clamp 10 each have an opening that allows the rod 40 to pass through. A bushing 50 may be used. The bushing 50 may surround the rod 40 and fit into the opening in the upper handle 12a.

The circle clamp 20 includes an upper portion 22 and a lower portion 24 connected to form a single piece. The upper portion 22 and lower portion 24 are connected at a circular shaped fulcrum 26. The fulcrum 26 has a circular hole 28 in it. The hole 28 allows for the insertion of a retractor, rail, or other object (not shown). Except for the connection at the fulcrum 26, a gap exists between the upper portion 22 and lower portion 24 of the circle clamp 20. The gap allows the circle clamp 20 to be squeezed, tightening the grip on the object being held in the circle clamp 20. A spacer 60 may lie within this gap. Both the upper portion 22 and lower portion 24 of the circle clamp 20 have an opening through which the rod 40 may pass. The opening in the lower portion 24 may fit the same bushing 50 that engages the scissors clamp 10.

Figure 4:
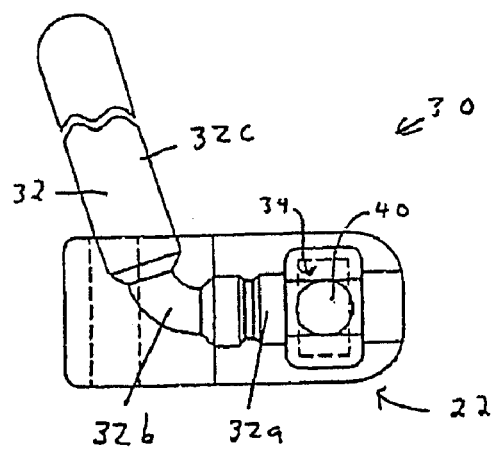
FIG. 4 is a top view, in partial cross-section of an embodiment of a cam locking mechanism of the present invention.
Figure 5:
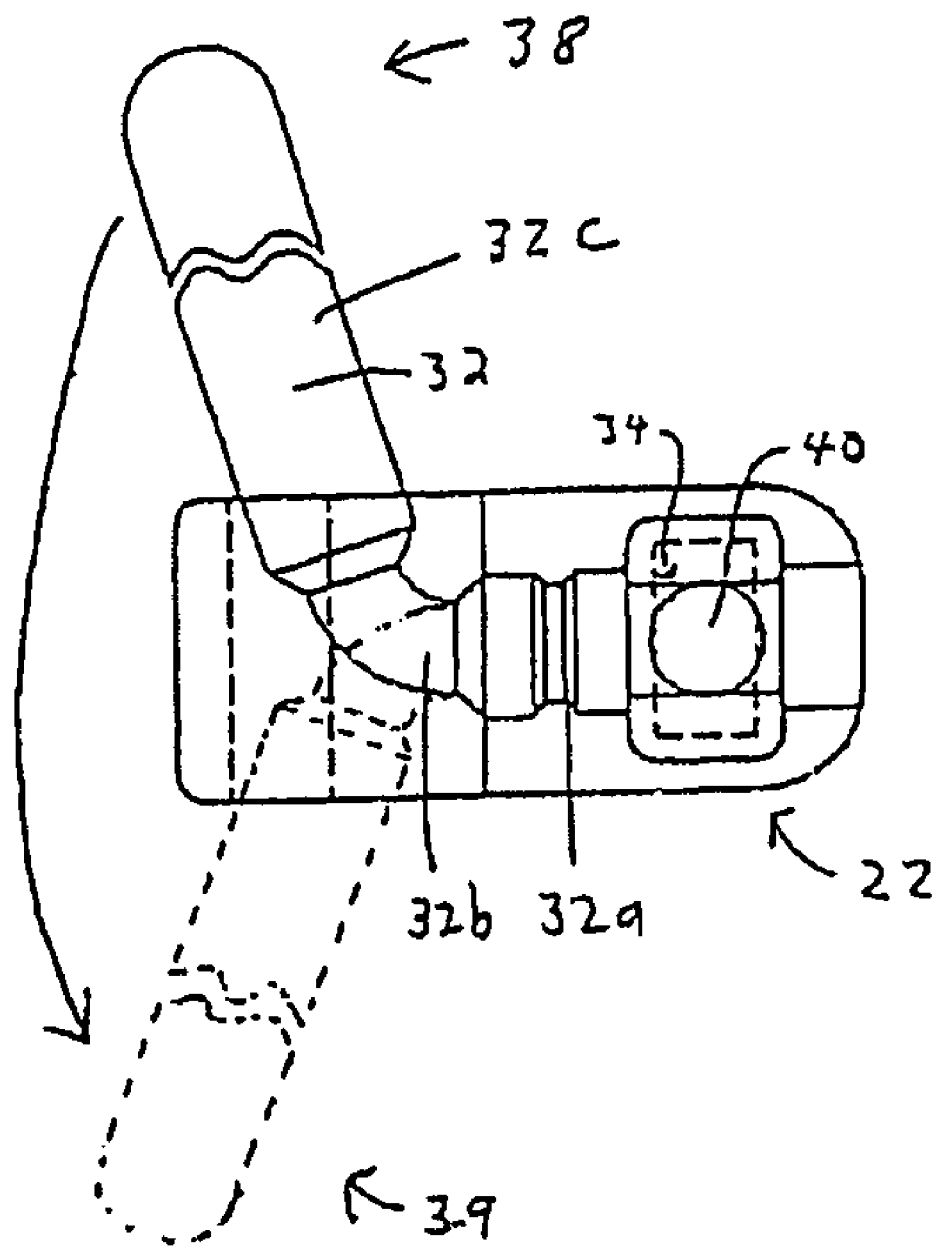
FIG. 5 is a side view, in partial cross-section of an embodiment of a cam locking mechanism and rod of the present invention.

Referring to FIGS. 1, 4, and 5, the locking mechanism 30 includes a handle 32 connected to a cam 34. The handle 32 consists of a first straight portion 32a, an elbow 32b, and a second straight portion 32c. The first straight portion 32a projects straight out from the cam 34, then the elbow 32b curves at an angle before the second straight portion 32c projects straight out from the elbow 32b. The second straight portion 32c of the handle 32 includes a recessed area 36. The cam 34 may be shaped asymmetrically with respect to the center axis 33 of the handle, so that the cam's center axis 35 is not aligned with the handle's center axis 33. The cam 34 is positioned through an eyehole 42 in the rod 40. Alternatively, the cam's center axis 35 may be aligned with the handle's center axis 33 where the cam 34 is not circular but instead has different radial lengths along different points of its perimeter, as will be appreciated by those skilled in the art.

Referring to FIGS. 3 and 5, the rod 40 associates the scissors clamp 10, circle clamp 20 and the cam locking mechanism 30. The rod 40 has an eyehole 42 at one end through which the cam 34 may be inserted. At the opposite end, the rod 40 may be connected to a nut 70. A spring 80 surrounds the rod 40 between the nut 70 and the lower handle 14a of the scissors clamp 10. Alternatively, the rod 40 may be directly attached to the lower handle 14a of the scissors clamp 10.

Figure 6:
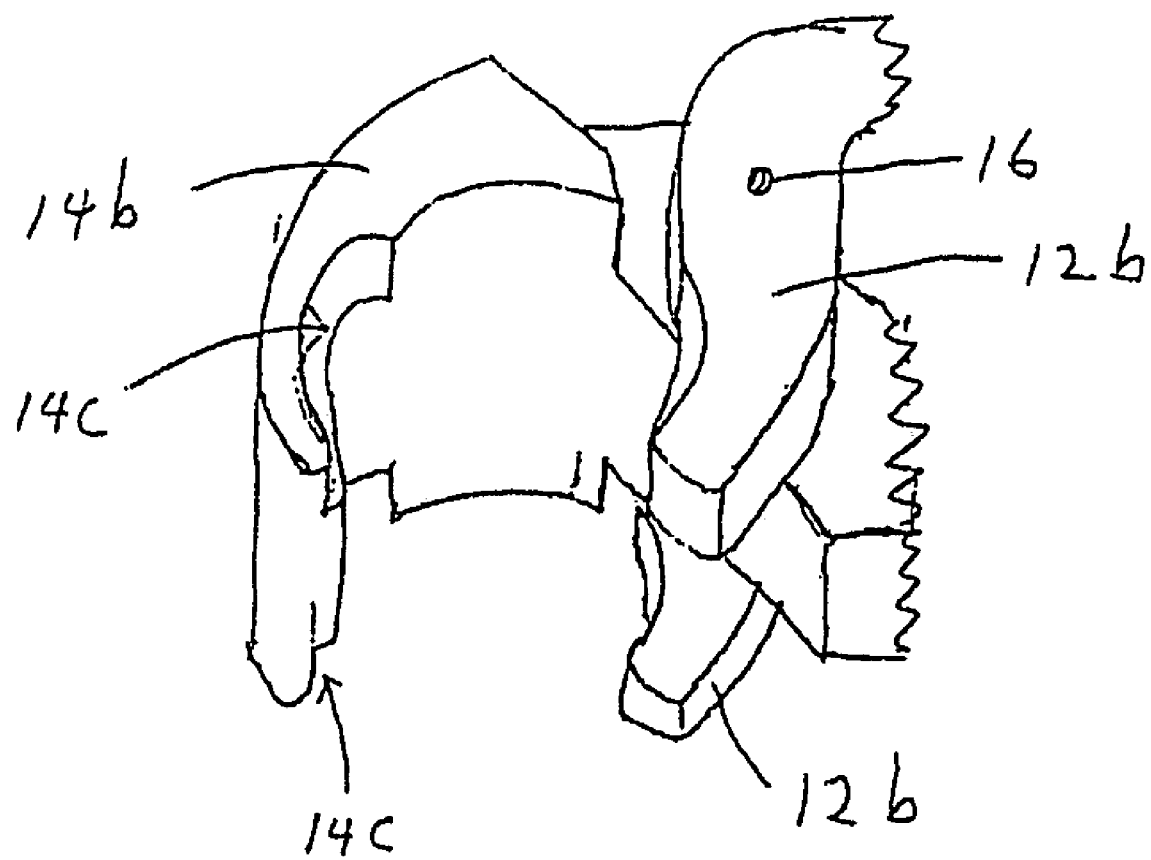
FIG. 6 is a top view, in partial cross-section, illustrating the operation of locking and unlocking an embodiment of the present invention.

Referring to FIGS. 3, 5, and 6, the universal scissors joint is engaged by rotating the cam handle 32 from an open position 38 to a locked position 39. Rotating the cam handle 32 rotates the cam 34 within the eyehole 42. This pushes the rod 40 upward, which causes the nut 70 and spring 80 to press upward on the lower handle 14a of the scissors clamp 10. Because the upper handle 12a of the scissors clamp 10 is connected by the bushing 50 to the lower portion 24 of the circle clamp 20, and the circle clamp 20 is a single piece, as the nut 70 and spring 80 move upward, both the scissors clamp 10 and the circle clamp 20 are squeezed, creating a tighter grip on the objects being held within the clamps.

Referring to FIGS. 1, 3, 5, and 6 the scissors clamp 10 and the circle clamp 20 are able to rotate with respect to each other. This allows any attached rods or surgical devices to be positioned in any manner desired for surgery. The ability to rotate may be locked or unlocked by the locking mechanism 30. When the cam handle 32 is in the open position 38, the scissors clamp 10 and the circle clamp 20 are able to freely rotate with respect to each other. When the cam handle 32 is in the locked position 39, the ability of the two clamps to rotate with respect to each other is made extremely difficult, with the result establishing a fixed position for the clamps with respect to each other so long as the cam handle 32 is in the locked position 39. As the cam handle 32 is rotated into the locked position 39, the upper handle 12a of the scissors clamp 10 is pressed against the bushing 50 with greater force, and the lower portion 24 of the circle clamp 20 is also pressed against the bushing 50 with greater force. This greater force creates greater friction between the scissors clamp 10 and the bushing 50 and between the circle clamp 20 and the bushing 50, greatly restricting the ability of the scissors clamp 10 and the circle clamp 20 to rotate with respect to each other.

Figure 7:
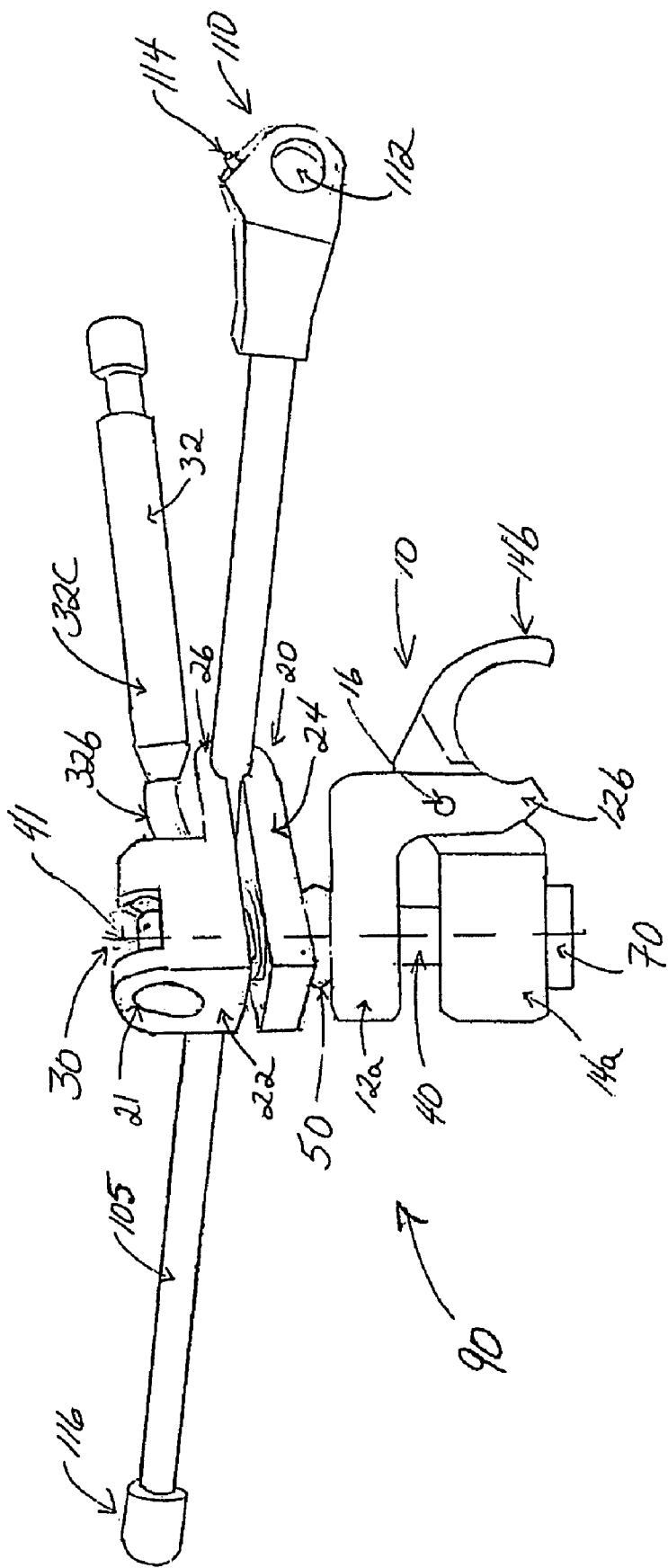
FIG. 7 is a perspective view of one embodiment of the invention in which a retractor blade handle is integrated into the universal joint.
Figure 8:
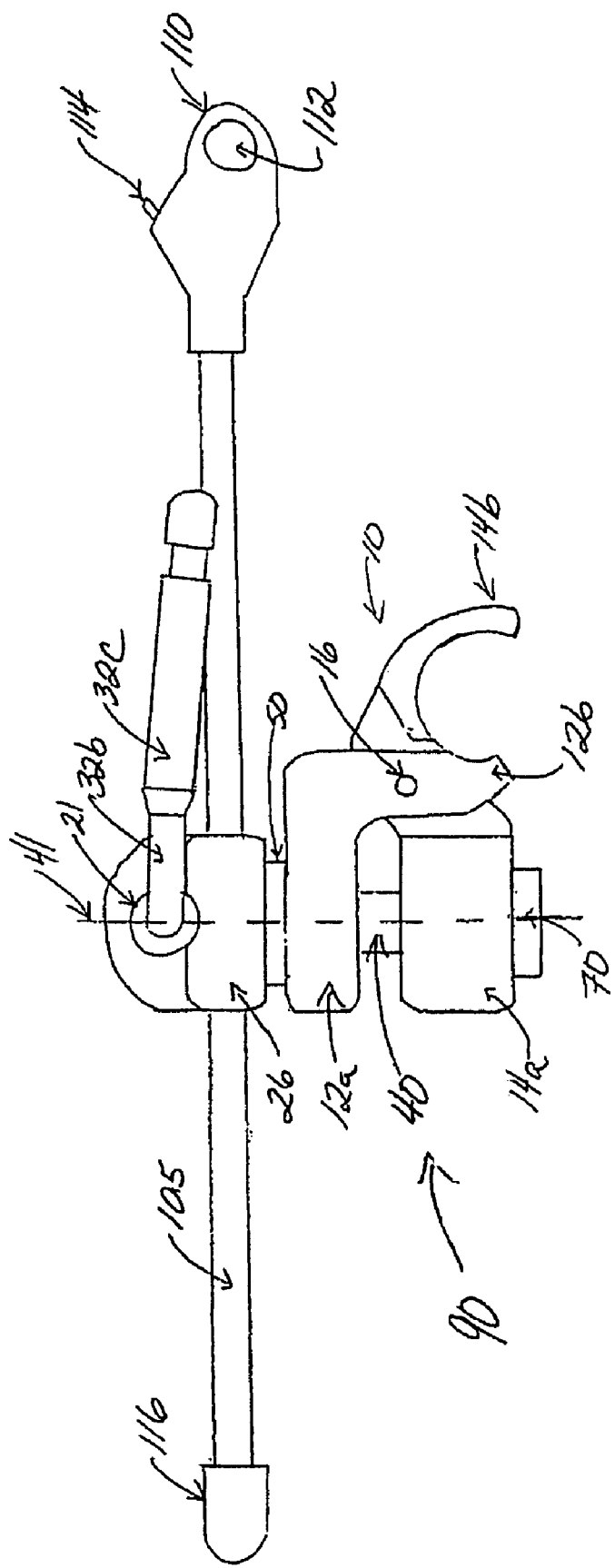
FIG. 8 is a side view of one embodiment of the invention in which a retractor blade handle is integrated into the universal joint.

FIGS. 7 and 8 illustrate an embodiment of the invention in which a dedicated retractor blade handle 105 is permanently mounted into the universal joint 90. The handle 105, passes through the circular hole 28 of the circle clamp 20. In the illustrated embodiment, the handle 105 has a head member 110 and an end cap 116, the head member 110 and end cap 116 being configured so that they are incapable of passing through the circular hole 28, thereby preventing the handle 105 from being removed from the universal joint 90.

FIGS. 7 and 8 also illustrate the cam locking mechanism 30 as being integrated into the universal joint 90. More specifically, the cam handle 32, cam 34, and eyehole 42 are illustrated as being located in the upper portion 22 of the circle clamp 20, with at least a portion of the cam handle 32 passing through, and rotating about, the orifice 21 of the upper portion 22. The rotational engagement of at least a portion of the cam handle 32 with the orifice 21 prevents the cam locking mechanism 30 from being swiveled and/or rotated about the longitudinal axis 41 of the rod 40 independently of the position of the circular clamp 20. Therefore, the orientation of the open position 38 or locked position 39 of the cam handle 32 always retains its position relative to the longitudinal axis of the circular hole 28.

Figure 9:
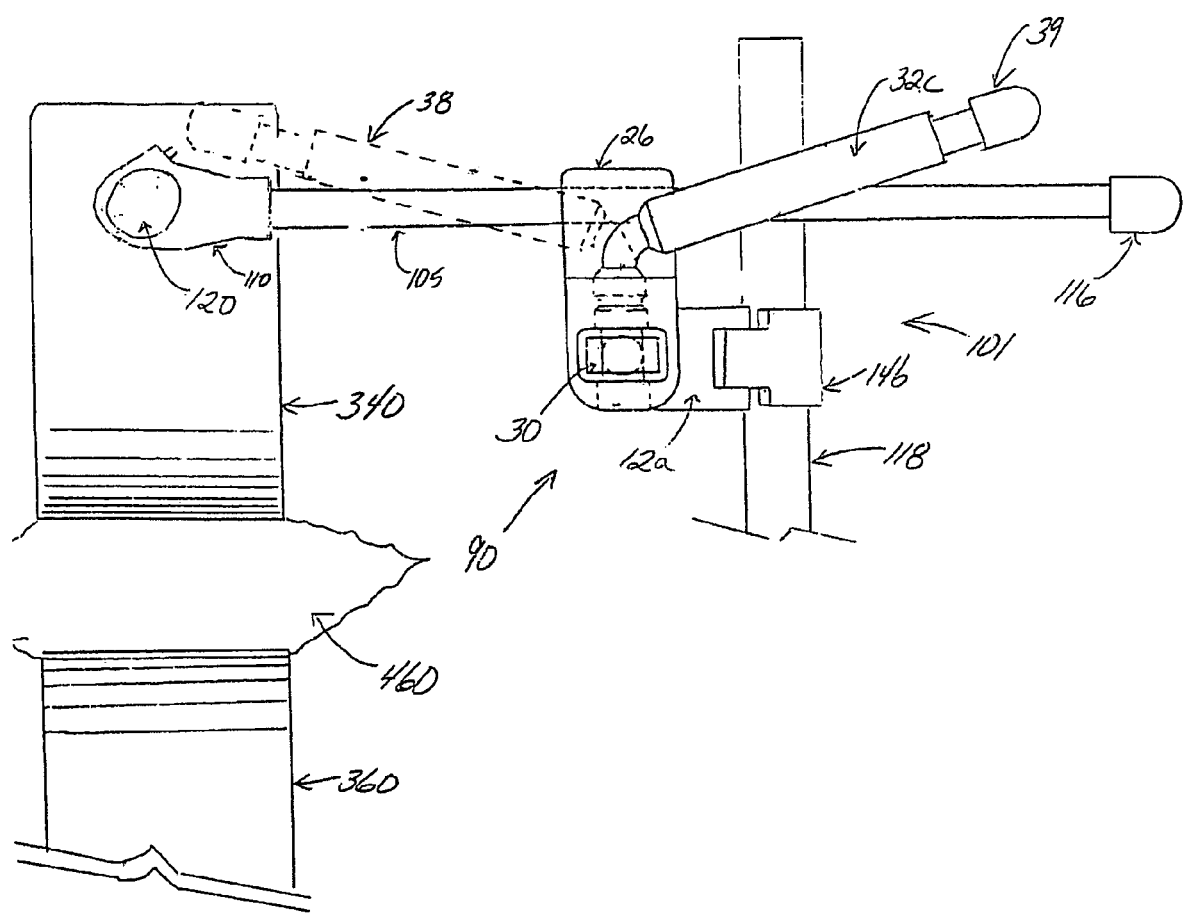
FIG. 9 is a top view of a portion of a retraction system, the illustrated embodiment of the invention including an integrated retractor blade handle that is attached to a retractor blade.

FIG. 9 illustrates a benefit of using an integrated handle 105. Scissors clamp 10 is shown attached to an extension arm 118. In this illustrated embodiment, because the handle 105 may not be removed from the universal joint 90, the head 110 of the handle 105, and associated retractor blade 340, may be assembled so that the cam handle 32 may only be manipulated from an open position 38, as illustrated by phantom lines, to a locked position 39, as illustrated by solid lines, to a position that is oriented substantially away from the incised opening 460 in the patient's anatomy, thereby providing an easy and efficient means of ensuring that the cam handle 32 does not interfere with the surgeon's visual contact with patient's anatomy or impair the surgeon's movement.

In the illustrated embodiment, the open position 38 and locked position 39 of cam handle 32 is illustrated as being substantially parallel with the handle 105. This reduces potential interference that may be associated with a cam handle 32 that substantially protrudes away from the retractor blade handle 105. The longitudinal axis of the cam handle is slightly angled away from the longitudinal axis of the retractor blade handle 105 so that the retractor blade handle 105 does not interfere with the ability to hold and manipulate the orientation of the cam handle 42.

Although the present invention has been described in considerable detail with reference to certain preferred versions thereof, other versions are possible. For example, types of clamps other than the circle clamp 20 may be used in conjunction with the scissors clamp 10, and more than two clamps may be used in one device. It will be appreciated that different sizes and shapes of the clamps may be used without departing from the scope of the present invention. Different types of cam locking mechanisms may be used, such as that revealed in U.S. Pat. No. 5,888,197. Still other types of locking mechanisms may be employed, such as a threaded locking mechanism. It will be appreciated that the handle and the cam may assume different shapes without departing from the scope of the present invention. It will be appreciated that the positions that constitute the locked and unlocked position may be changed without departing from the scope of the present invention. The revealed embodiment is not able to be completely disassembled, so as to allow sterilization without disassembly, but other embodiments may be completely disassembled. Therefore, the spirit and scope of the appended claims should not be limited to the description of the preferred versions contained herein.

What is claimed is:

1. A universal joint apparatus for a surgical retraction system comprising:

a scissors clamp having a first segment, a second segment, and a pivot, the first segment being a first unitary structure and having a first handle and two lower grippers, the second segment being a second unitary structure and having a second handle and an upper gripper, the unitary structures of the first and second segments being mechanically fastened to each other by the pivot, one segment being configured to cross the other segment at the pivot, the first handle and second handle being located on the first side of the pivot, the first handle being separated from the second handle by a gap, the two lower grippers and the upper gripper being located on the second side of the pivot, the upper gripper and the lower grippers being oriented to create a passageway between the upper and lower grippers that is configured to receive the insertion of a retractor blade handle; wherein each of the two lower grippers is positioned adjacent to an opposing side of a portion of the second segment on the second side of the pivot, and a locking mechanism and a rod, the rod associating the locking mechanism with the scissors clamp, the manipulation of the locking mechanism enabling the scissors clamp to be moved from an open position to a locked position wherein the size of both the gap between the first handle and the second handle and the size of the passageway between the upper gripper and the lower grippers are reduced so as to provide a compressive force on the retractor blade handle.

2. The apparatus of claim 1, further comprising a clamping member.

3. The apparatus of claim 2, wherein the clamping member has a dedicated retractor blade handle.

4. The apparatus of claim 2, wherein the scissors clamp and the the clamping member are independently rotatable with respect to each other.

5. The apparatus of claim 2, wherein the clamping member comprises an upper segment and a lower segment, said segments being parallel to each other;

having a space between them; and being joined at one end.

6. The apparatus of claim 2 wherein the locking mechanism comprises:

a handle; and a cam connected to the handle and engaging the rod so that the cam operates the scissors clamp and the clamping member when selectively positioned by the handle.

7. The apparatus of claim 6 wherein the rod includes an eyehole through which the cam may be inserted.

8. The apparatus of claim 6, wherein the clamping member has a dedicated retractor blade handle, the cam locking mechanism having an open position and a locked position, the orientation of the cam handle in the locked position being substantially parallel to the retractor blade handle.

9. The apparatus of claim 8, wherein the orientation of the locked position of the cam handle extends substantially away from an operative site.

10. The apparatus of claim 1, wherein at least a portion of the upper gripper includes indentations.

11. A universal joint apparatus comprising:
a scissors clamp having a first segment, a second segment, and a pivot, the first segment being a first unitary structure and having a first handle and two lower grippers, the second segment being a second unitary structure and having a second handle and an upper gripper, the first handle being separated from the second handle by a gap, a portion of the first segment being mechanically fastened to the second segment by the pivot, each of the two lower grippers positioned adjacent to an opposing side of a portion of the second segment, a portion of the upper gripper and the lower grippers being oriented to create a passageway between the upper and lower grippers that is configured to receive the insertion of a retractor blade handle;
a first clamping member;
a locking mechanism and a rod, the rod associating the locking mechanism with the scissors clamp, the manipulation of the locking mechanism enabling the scissors clamp to be moved from an open position to a locked position wherein the size of both the gap between the first handle and the second handle and the passageway between the upper gripper and the lower grippers are reduced so as to provide a compressive force on the retractor blade handle.

12. The apparatus of claim 11, further comprising a second clamping member.

13. The apparatus of claim 12, wherein the scissors clamp and the second clamping member are independently rotatable with respect to each other.

14. The apparatus of claim 12, wherein the second clamping member comprises an upper segment and a lower segment, said segments
being parallel to each other;
having a space between them; and
being joined at one end.

15. The apparatus of claim 12, wherein the second clamping member has a dedicated retractor blade handle.

16. The apparatus of claim 12 wherein the locking mechanism comprises:
a handle; and
a cam connected to the handle and engaging the rod so that the cam operates the first clamping member and the additional clamping members when selectively positioned by using the handle.

17. The apparatus of claim 16 wherein the rod includes an eyehole through which the cam may be inserted.

18. The apparatus of claim 16, wherein the second clamping member has a dedicated retractor blade handle, the cam locking mechanism having an open position and a locked position, the orientation of the cam handle in the locked position being substantially parallel to the retractor blade handle.

19. The apparatus of claim 18, wherein the orientation of the locked position of the cam handle extends substantially away from an operative site.

20. The apparatus of claim 11, wherein at least a portion of the upper gripper includes indentations.

21. A universal joint apparatus comprising:
a scissors clamp having a first segment, a second segment, and a pivot, the first segment being a first unitary structure and having a first handle and two lower grippers, the second segment being a second unitary structure and having a second handle and an upper gripper, the first segment and second segment being mechanically fastened to each other by the pivot, one segment being configured to cross the other segment at the pivot, the first handle and second handle being located on the first side of the pivot, the first handle being separated from the second handle by a gap, the two lower grippers and the upper gripper being located on the second side of the pivot, the upper gripper and the lower grippers being oriented to create a passageway between the upper and lower grippers that is configured to receive the insertion of a retractor blade handle; wherein each of the two lower grippers is positioned adjacent to an opposing side of a portion of the second segment, and
a second clamping member, the second clamping member having a dedicated retractor blade handle, the second clamping member and the scissors clamp being independently rotatable with respect to each other;
a cam locking mechanism comprising a handle and a cam, the cam operably connected to the handle, the cam locking mechanism having an open position and a locked position, the orientation of the cam handle in the locked position being substantially parallel to the retractor blade handle; and
a rod associating the cam locking mechanism, the first clamping member, and the second clamping member, the rod having an eyehole configured for engagement with the cam so that the cam operates the first clamping member and the second clamping member when selectively positioned by the handle, the manipulation of the cam locking mechanism enabling the scissors clamp to be moved from an open position to a locked position wherein the size of both the gap between the first handle and the second handle and the passageway between the upper gripper and the lower grippers are reduced so as to provide a compressive force on the retractor blade handle.

22. The apparatus of claim 21, wherein the second clamping member comprises an upper segment and a lower segment, said segments
being parallel to each other;
having a space between them; and
being joined at one end.

23. The apparatus of claim 21, wherein at least a portion of the upper gripper includes indentations.

24. The apparatus of claim 21, wherein the orientation of the locked position of the cam handle extends substantially away from an operative site.

* * * * *